United States Patent
Chen (10) Patent No.: US 10,798,971 B2
(45) Date of Patent: Oct. 13, 2020

(54) FIXING STRUCTURE AND ELECTRONIC CIGARETTE HAVING SAME

(71) Applicant: SHENZHEN IVPS TECHNOLOGY CO., LTD., Shenzhen, Guangdong Province (CN)

(72) Inventor: Wen Chen, Shenzhen (CN)

(73) Assignee: SHENZHEN IVPS TECHNOLOGY CO., LTD., Shenzhen (CN)

( * ) Notice: Subject to any disclaimer, the term of this patent is extended or adjusted under 35 U.S.C. 154(b) by 365 days.

(21) Appl. No.: 15/879,451

(22) Filed: Jan. 25, 2018

(65) Prior Publication Data

US 2018/0146714 A1 May 31, 2018

(30) Foreign Application Priority Data

Nov. 28, 2016 (CN) .................... 2016 2 1286941 U (51) Int. Cl.
*A24F 47/00* (2020.01)
*A61M 15/06* (2006.01)
*H01R 13/22* (2006.01)
*H05B 1/02* (2006.01)

(52) U.S. Cl.
CPC ........... *A24F 47/008* (2013.01); *A61M 15/06* (2013.01); *H01R 13/22* (2013.01); *A61M 2205/50* (2013.01); *A61M 2205/8206* (2013.01); *A61M 2207/00* (2013.01); *H05B 1/0297* (2013.01)

(58) Field of Classification Search
CPC .................................................. A24F 47/008
See application file for complete search history.

(56) References Cited

U.S. PATENT DOCUMENTS

| | | | |
|---|---|---|---|
| 2006/0215408 A1* | 9/2006 | Lee ........................ | F21V 29/773 362/294 |
| 2007/0215324 A1* | 9/2007 | Chen ...................... | H01L 23/473 165/80.4 |
| 2009/0141461 A1* | 6/2009 | Chen ....................... | H05K 7/142 361/752 |
| 2012/0113598 A1* | 5/2012 | Toh ....................... | H01L 23/4006 361/715 |
| 2016/0286861 A1* | 10/2016 | Liu ........................ | A24F 47/008 |
| 2018/0014429 A1* | 1/2018 | Ju ........................ | H05K 7/20445 |
| 2018/0146714 A1* | 5/2018 | Chen ...................... | H01R 13/22 |
| 2018/0206555 A1* | 7/2018 | Chen ........................ | H05B 3/04 |
| 2018/0279514 A1* | 9/2018 | Maemuko ............ | H05K 1/0215 |

(Continued)

*Primary Examiner* — James Harvey
(74) *Attorney, Agent, or Firm* — IP-PAL Patent US; Klaus Michael Schmid (57) ABSTRACT

The present disclosure provides a PCB fixing structure. The PCB fixing structure includes a housing, a PCB accommodated in the housing, and a top cap covering the housing. The housing has a side wall provided with at least two protrusion portions. The protrusion portion defines a connecting hole. The PCB defines at least two first through holes. The top cap defines at least two second through holes. The PCB fixing structure further includes at least two connecting pieces. Each of the connecting pieces is configured to pass through one of the second through holes, one of the first through holes and one of the connecting holes in sequence so as to fix the top cap and the PCB to the housing. The present disclosure further provides an electronic cigarette including the PCB fixing structure and a fixing structure for a PCBA control board of an electronic cigarette.

10 Claims, 4 Drawing Sheets

(56) References Cited

U.S. PATENT DOCUMENTS

2018/0310617 A1\* 11/2018 Ding .................. A24F 40/40
2019/0191765 A1\* 6/2019 Chen ................. A24F 47/008
2020/0008467 A1\* 1/2020 Ouyang ............ A24F 47/008

\* cited by examiner

FIXING STRUCTURE AND ELECTRONIC CIGARETTE HAVING SAME

CROSS REFERENCE TO RELATED APPLICATIONS

The present application claims priority to Chinese Patent Application CN 201621286941.7 filed on Nov. 28, 2016.

TECHNICAL FIELD

The present disclosure relates to the technical field of electronic cigarettes, and in particular to a Printed Circuit Board (PCB) fixing structure, a fixing structure for a printed circuit board assembly (PCBA) control board, and an electronic cigarette having the same fixing structure.

BACKGROUND

An electronic cigarette includes a PCB. Generally, the way to secure the PCB is to mount the PCB on a support inside the electronic cigarette. Since it is needed to add a support, the cost of the electronic cigarette is increased and the production efficiency of the electronic cigarette is lowered.

In the prior art, electronic cigarettes have a PCBA control board and a fixing part connected fixedly through screws. However, when fixing the PCBA control board and the fixing part of the electronic cigarettes using screws, it is needed to define corresponding threaded holes and reserve a space for nuts in a wiring forbidden area of the PCBA control board. The operation of defining threaded holes and reserving a space for nuts in the wiring forbidden area of the PCBA control board increases indirectly the area of the PCBA control board. As a result, the electronic cigarette becomes relatively big in size and is aesthetic impacting.

SUMMARY

The present disclosure mainly aims to provide a PCB fixing structure, so as to lower the cost and improve the assembly efficiency.

In order to achieve the above aim, the PCB fixing structure provided by the present disclosure includes a housing, a PCB accommodated in the housing, and a top cap covering the housing. The housing has a side wall provided with at least two protrusion portions. The protrusion portion defines a connecting hole. The PCB defines at least two first through holes. The top cap defines at least two second through holes.

The PCB fixing structure further includes at least two connecting pieces. Each of the connecting pieces is configured to pass through one of the second through holes, one of the first through holes and one of the connecting holes in sequence so as to fix the top cap and the PCB to the housing.

Preferably, the PCB includes a first PCB and a second PCB connected to the first PCB, the first PCB and the second PCB are configured to be arranged opposite each other in parallel, the first PCB defines at least two of the first through holes, the second PCB defines at least two notches fitting the protrusion portion at corresponding positions, the protrusion portion is configured to pass through the notch, and the first PCB is configured to be connected to a top end of the protrusion portion.

Preferably, the housing has two opposing side walls provided with a limiting column respectively, the PCB has an edge defining a plurality of limiting grooves, and each of the limiting columns is configured to be partially accommodated in the limiting groove.

Preferably, the PCB is provided with a USB interface at one end thereof, and the housing defines an opening matched with the USB interface at a corresponding position.

Preferably, the PCB is provided with a display on one side close to the top cap, and the top cap is provided with a transparent lens at a position corresponding to the display.

Preferably, the top cap is further provided with a conducting ring in a convex way at a position far away from the transparent lens, the conducting ring is configured to be in electric connection with the PCB, the PCB defines a mounting hole, and the conducting ring is configured to be partially accommodated in the mounting hole.

Preferably, the second through hole has a hole wall extending in the direction towards the PCB to form a screw stud, the screw stud is configured to abut against the PCB, the top cap and the PCB form an accommodation portion therebetween, and the display is configured to be accommodated in the accommodation portion.

The present disclosure further provides an electronic cigarette. The electronic cigarette includes the PCB fixing structure described above. The electronic cigarette further includes an atomization assembly and a big copper part connected to the atomization assembly. The top cap is provided with a conducting ring in a convex way. The top cap defines a hole at a position corresponding to the conducting ring. The big copper part is configured to pass through the hole to be partially accommodated in the conducting ring.

Preferably, the big copper part is configured to be in electric connection with the conducting ring, and the conducting ring is configured to be in electric connection with the PCB.

Preferably, the electronic cigarette further includes a battery, and the battery is configured to be connected to one side of the PCB and accommodated in the housing.

According to the technical scheme of the present disclosure, the PCB is mounted to the protrusion portion on the side wall of the housing, so that an internal support is avoided. Moreover, the top cap and the PCB are fixed on the housing simultaneously through one connecting piece, so that the production cost of the electronic cigarette is lowered and the assembly efficiency of the electronic cigarette is improved.

The present disclosure mainly aims to provide a fixing structure for a PCBA control board of an electronic cigarette, so as to reduce the area of the PCBA control board of the electronic cigarette and then to reduce the size of the electronic cigarette.

In order to achieve the above aim, the present disclosure provides a fixing structure for a PCBA control board of an electronic cigarette. The fixing structure includes a PCBA control board and a fixing part configured for fixing the PCBA control board. The PCBA control board is configured to be in fixed connection with the fixing part through a conducting nail. The conducting nail is configured to be in electric connection with an output negative electrode of the PCBA control board.

Preferably, the fixing part defines a clamping groove configured for clamping the PCBA control board, the PCBA control board is provided with a projecting portion fitting the clamping groove, and the projecting portion is configured to be clamped in the clamping groove of the fixing part.

Preferably, the projecting portion defines a through hole fitting the conducting nail, the clamping groove has a bottom surface defining a blind hole fitting the conducting nail at a position directly opposite the through hole, and the conducting nail is configured for fixing the PCBA control board to the fixing part via the through hole and the blind hole.

Preferably, the projecting portion is provided with a first tin layer on an end surface facing the bottom surface of the clamping groove, the through hole has an inner sidewall provided with a second tin layer, both the first tin layer and the second tin layer are configured to serve as the output negative electrode of the PCBA control board, and the output negative electrode is configured to be in electric connection with the fixing part.

Preferably, the conducting nail is provided with a third tin layer on a top thereof, and the third tin layer is configured for fastening and welding the conducting nail to the PCBA control board.

Preferably, the number of the conducting nails, the number of the projecting portions, the number of the clamping grooves, the number of the through holes, and the number of the blind holes are two respectively; the projecting portions are configured to be arranged opposite each other at two sides of the PCBA control board; and the clamping grooves are configured to be arranged opposite each other at two sides of the fixing part.

Preferably, the fixing structure further includes a positive electrode contact component fixed on the fixing part, and the PCBA control board has a positive electrode output wire welded to the positive electrode contact component.

Preferably, the conducting nail is made of copper materials.

In order to achieve the above aim, the present disclosure further provides an electronic cigarette. The electronic cigarette includes the fixing structure described above.

The present disclosure provides a fixing structure for a PCBA control board of an electronic cigarette. The fixing structure includes a PCBA control board and a fixing part configured for fixing the PCBA control board. The PCBA control board is configured to be in fixed connection with the fixing part through a conducting nail. The conducting nail is configured to be in electric connection with an output negative electrode of the PCBA control board. According to the present disclosure, the area of the PCBA control board of the electronic cigarette can be reduced, and then the size of the electronic cigarette can be reduced; thus, the electronic cigarette gets a better appearance.

BRIEF DESCRIPTION OF THE DRAWINGS

For a better understanding of the technical scheme in the embodiments of the present disclosure or in the prior art, accompanying drawings needed in the description of the embodiments or the prior art are simply illustrated below. Obviously, the accompanying drawings described below are some embodiments of the present disclosure. For the ordinary skill in the field, other accompanying drawings may be obtained according to the structure shown in these accompanying drawings without creative work.

DESCRIPTION OF REFERENCE NUMBERS

| Reference number | Name of Part | Reference number | Name of Part |
|---|---|---|---|
| 100 | PCB fixing structure 100 | 36 | USB interface |
| 10 | Housing | 37 | Notch |
| 11 | Protrusion portion | 38 | Mounting hole |
| 15 | Limiting column | 50 | Connecting piece |
| 17 | Opening | 70 | Top cap |
| 30 | PCB | 71 | Transparent lens |
| 31 | First through hole | 72 | Second through hole |
| 32 | Display | 73 | Conducting ring |
| 33 | Limiting groove | 74 | Screw stud |
| 34 | First PCB | 75 | Hole |
| 35 | Second PCB | 4 | Positive electrode contact component |
| 1 | Conducting nail | 3 | Fixing part |
| 2 | PCBA control board | 31a | Clamping groove |
| 21 | Projecting portion | 32a | Blind hole |
| 22 | Through hole | | |

The implementation of aims, the function features and the advantages of the present disclosure are described below in further detail in conjunction with embodiments with reference to the drawings.

DETAILED DESCRIPTION

A clear and complete description as below is provided for the technical scheme in the embodiments of the present disclosure in conjunction with the drawings in the embodiments of the present disclosure. Obviously, the embodiments described hereinafter are simply part embodiments of the present disclosure, but all the embodiments. All other embodiments obtained by the ordinary skill in the art based on the embodiments in the present disclosure without creative work are intended to be included in the scope of protection of the present disclosure.

It should be noted that all directional indications (such as top, bottom, left, right, front, behind . . . ) in the embodiments of the present disclosure are merely to illustrate a relative position relation, a relative motion condition, etc. between each part in a certain state (for example, the state shown in the drawings). If the state changes, the directional indication changes accordingly.

In addition, terms "first", "second", etc. appearing in the present disclosure are merely for the purpose of description, but cannot be understood as the indication or implication of relative importance or as the implicit indication of the number of the designated technical features; therefore, features defined by "first" and "second" may specifically or implicitly include at least one such feature. In addition, technical schemes of each embodiment of the present disclosure can be combined mutually; however, this must be carried out on the basis that the ordinary skill in this field can implement the combination. When the combination of technical schemes has a conflict or cannot be implemented, it should be considered that such combination of technical schemes does not exist and is not in the scope of protection claimed by the present disclosure.

The present disclosure provides a PCB fixing structure.

Figure 1:
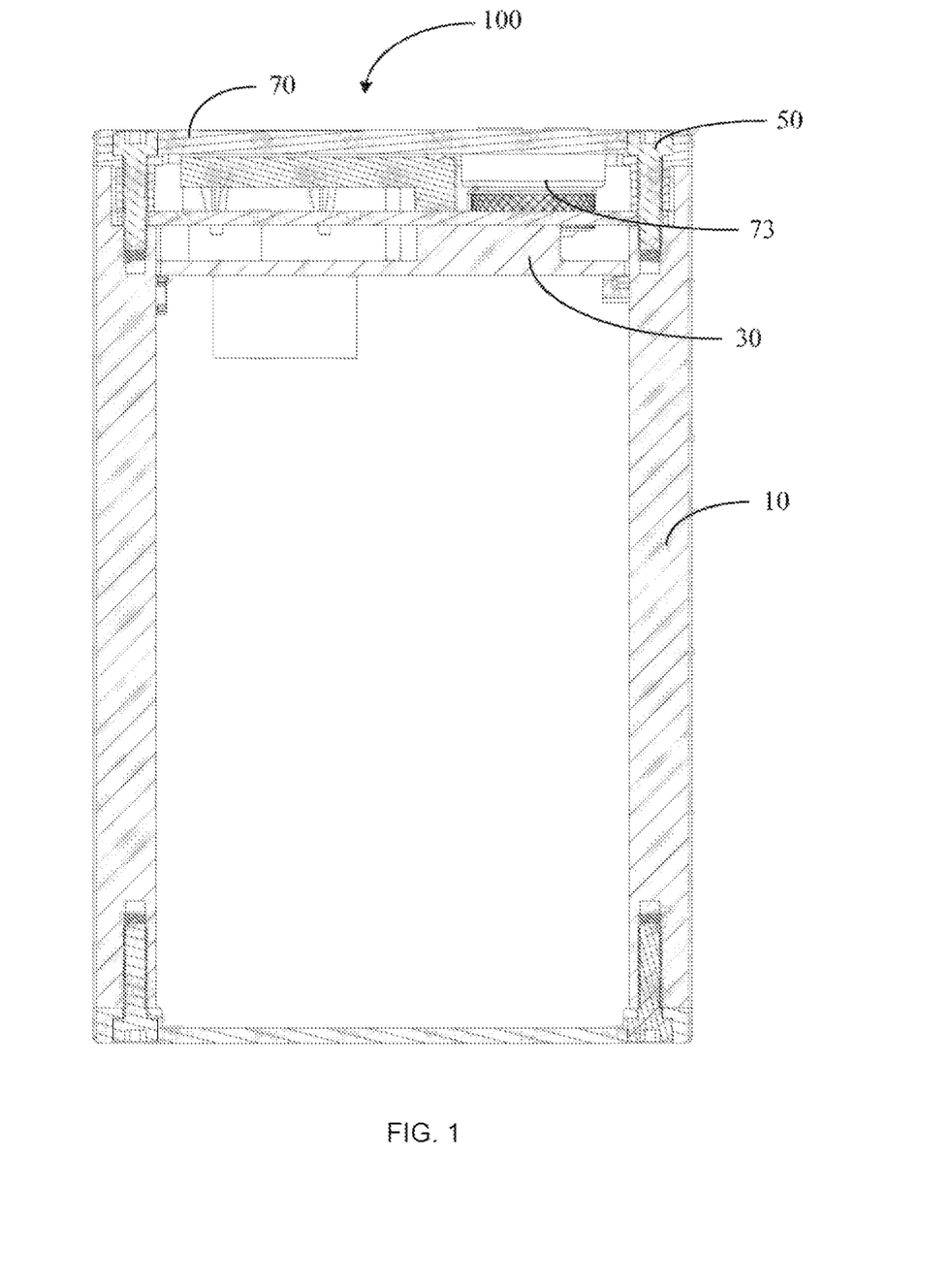
FIG. 1 is a structure diagram of an embodiment of a PCB fixing structure of the present disclosure.
Figure 2:
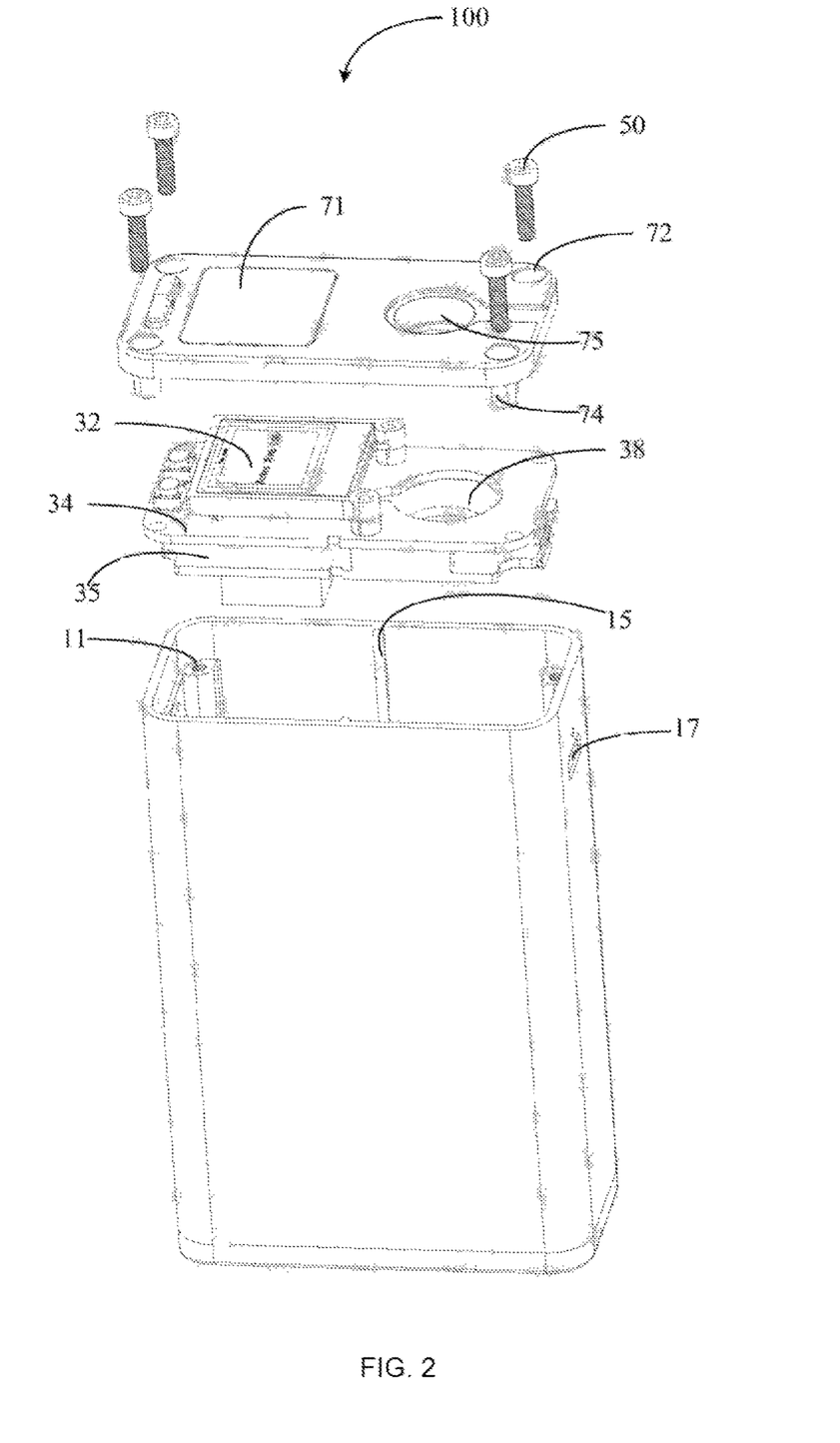
FIG. 2 is an exploded view of the PCB fixing structure.
Figure 3:
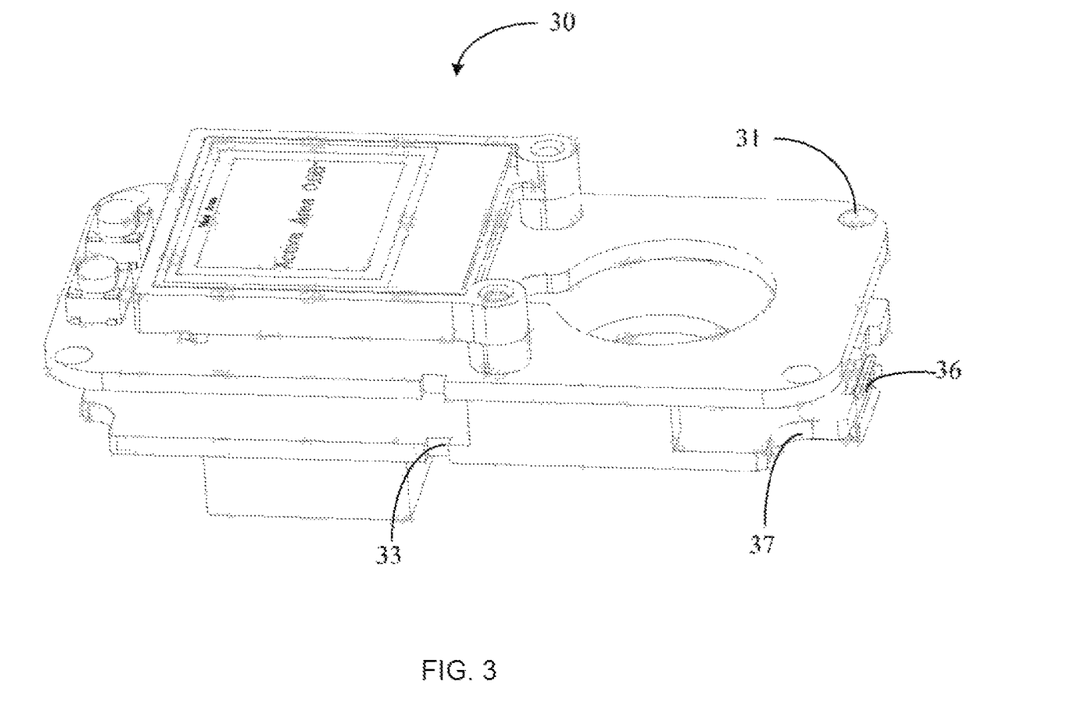
FIG. 3 is a structure diagram of the PCB shown in FIG. 2.
Figure 4:
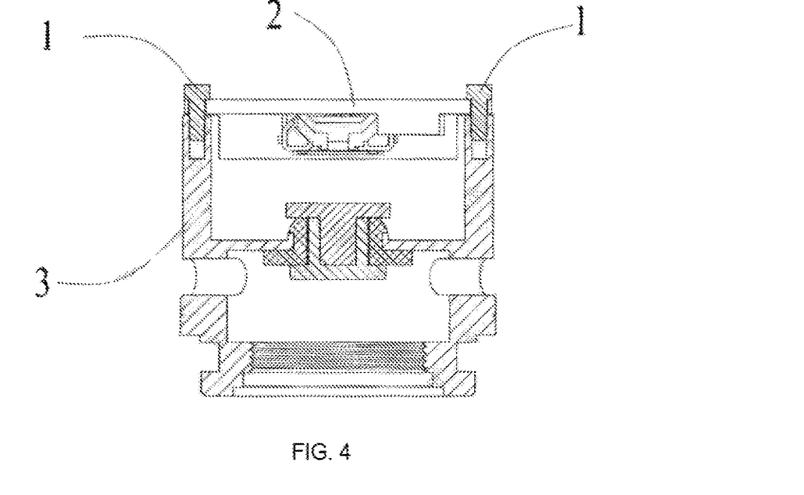
FIG. 4 is a longitudinal cross-sectional view of a fixing structure for a PCBA control board of an electronic cigarette of the present disclosure.

Referring to FIG. 1 to FIG. 3, FIG. 1 is a structure diagram of an embodiment of a PCB fixing structure of the present disclosure, FIG. 2 is an exploded view of the PCB fixing structure, and FIG. 3 is a structure diagram of the PCB shown in FIG. 2.

The PCB fixing structure 100 includes a housing 10, a PCB 30 accommodated in the housing 10, and a top cap 70 covering the housing 10. The housing 10 has a side wall provided with at least two protrusion portions 11. Preferably, the housing 10 is provided with four protrusion portions 11 at diagonal positions. The protrusion portion 11 defines a connecting hole. The connecting hole is provided with threads internally. The PCB 30 defines at least two first through holes 31. The top cap 70 defines at least two second through holes 72. The PCB fixing structure 100 further includes at least two connecting pieces 50. Each of the connecting pieces 50 is configured to pass through one of the second through holes 72, one of the first through holes 31 and one of the connecting holes in sequence so as to fix the top cap 70 and the PCB 30 to the housing 10.

According to the technical scheme of the present disclosure, the PCB 30 is mounted to the protrusion portion 11 on the side wall of the housing 10, so that an internal support is avoided. Moreover, the top cap 70 and the PCB 30 are fixed on the housing 10 simultaneously through one connecting piece 50, so that the production cost of the electronic cigarette is lowered and the assembly efficiency of the electronic cigarette is improved.

The PCB 30 includes a first PCB 34 and a second PCB 35 connected to the first PCB 34. The first PCB 34 and the second PCB 35 are configured to be arranged opposite each other in parallel. The first PCB 34 defines at least two of the first through holes 31. The second PCB 35 defines at least two notches 37 at corresponding positions. The protrusion portion 11 is configured to pass through the notch 37, and the first PCB 34 is configured to be connected to a top end of the protrusion portion 11. Specifically, the protrusion portion 11 and the notch 37 are configured to be in clearance fit, to facilitate the mounting of the PCB 30.

According to the technical scheme of the present disclosure, the PCB 30 includes the first PCB 34 and the second PCB 35 that are arranged in parallel, so that the effective layout area of the PCB 30 can be increased without enlarging the entire size of the electronic cigarette.

The housing 10 has two opposing side walls provided with a limiting column 15 respectively. Both the first PCB 34 and the second PCB 35 have an edge defining a plurality of limiting grooves 33. Each of the limiting columns 15 is configured to be partially accommodated in the limiting groove 33.

According to the technical scheme of the present disclosure, the housing is provided with the limiting column 15, and the PCB has the edge defining the limiting groove 33. The limiting column 15 and the limiting groove 33 are configured to fit each other, to facilitate the mounting and fixing of the PCB.

The PCB 30 is provided with a USB interface 36 at one end thereof, and the housing 10 defines an opening 17 matched with the USB interface 36 at a corresponding position.

According to the technical scheme of the present disclosure, the PCB 30 is provided with the USB interface 36 and the housing 10 defines the opening 17 at the corresponding position, so that the USB interface 36 can be connected to an external power supply or other equipment to charge and upgrade the electronic cigarette.

The PCB 30 is provided with a display 32 on one side close to the top cap 70, and the top cap 70 is provided with a transparent lens 71 at a position corresponding to the display 32. The display 32 is configured to be connected to a plurality of brackets. The bracket is configured to be welded on the PCB 30. Two brackets located in the middle of the PCB 30 define a hole. The top cap 70 is provided with a support column at a corresponding position. The support column is configured to be accommodated in the hole on the bracket. When assembling, the top cap 70 and the PCB 30 are fixed together and then are placed above the protrusion portion 11, and finally the connecting piece 50 is screwed in to fix the top cap 70 and the PCB 30 to the housing 10.

According to the technical scheme of the present disclosure, the PCB is further provided with the display 32, so that the usage state of the electronic cigarette can be displayed; and the top cap 70 is provided with the transparent lens 71, so that a user can observe conveniently.

The top cap 70 is further provided with a conducting ring 73 in a convex way at a position far away from the transparent lens 71, the conducting ring 73 is configured to be in electric connection with the PCB 30, the PCB 30 defines a mounting hole 38, and the conducting ring 73 is configured to be partially accommodated in the mounting hole 38.

According to the technical scheme of the present disclosure, the top cap 70 is provided with the conducting ring 73, and the conducting ring 73 is configured to connect the PCB 30 and other parts of the electronic cigarette.

The second through hole 72 has a hole wall extending in the direction towards the PCB 30 to form a screw stud 74. The screw stud 74 is configured to abut against the PCB 30. The top cap 70 and the PCB 30 define an accommodation portion therebetween. The display 32 is configured to be accommodated in the accommodation portion.

According to the technical scheme of the present disclosure, the top cap 70 is provided with the screw stud 74, and the screw stud 74 is configured to abut against the PCB 30, so that the top cap 70 and the PCB define therebetween a space configured to mount the display 32.

The present disclosure further provides an electronic cigarette. The electronic cigarette includes the PCB fixing structure 100 described above. The electronic cigarette further includes an atomization assembly and a big copper part connected to the atomization assembly. The specific structure of the PCB fixing structure 100 can be referred to the above embodiments. Since the present electronic cigarette employs all technical schemes of the above embodiment, the present electronic cigarette at least has all beneficial effects brought by the technical schemes of the above embodiments. No further description is needed here. The top cap 70 is provided with a conducting ring 73 in a convex way. The top cap 70 defines a hole 75 at a position corresponding to the conducting ring 73. The big copper part is configured to pass through the hole 75 to be partially accommodated in the conducting ring 73.

The big copper part is configured to be in electric connection with the conducting ring 73, and the conducting ring 73 is configured to be in electric connection with the PCB.

According to the technical scheme of the present disclosure, the conducting ring 73 is configured to connect the big copper part and the PCB.

The electronic cigarette further includes a battery. The battery is configured to be connected to one side of the PCB and accommodated in the housing 10.

According to the technical scheme of the present disclosure, the electronic cigarette includes the battery, and the battery is configured to be welded on the PCB 30 to supply power to the electronic cigarette.

The present disclosure provides a fixing structure for a PCBA control board of an electronic cigarette.

Figure 5:
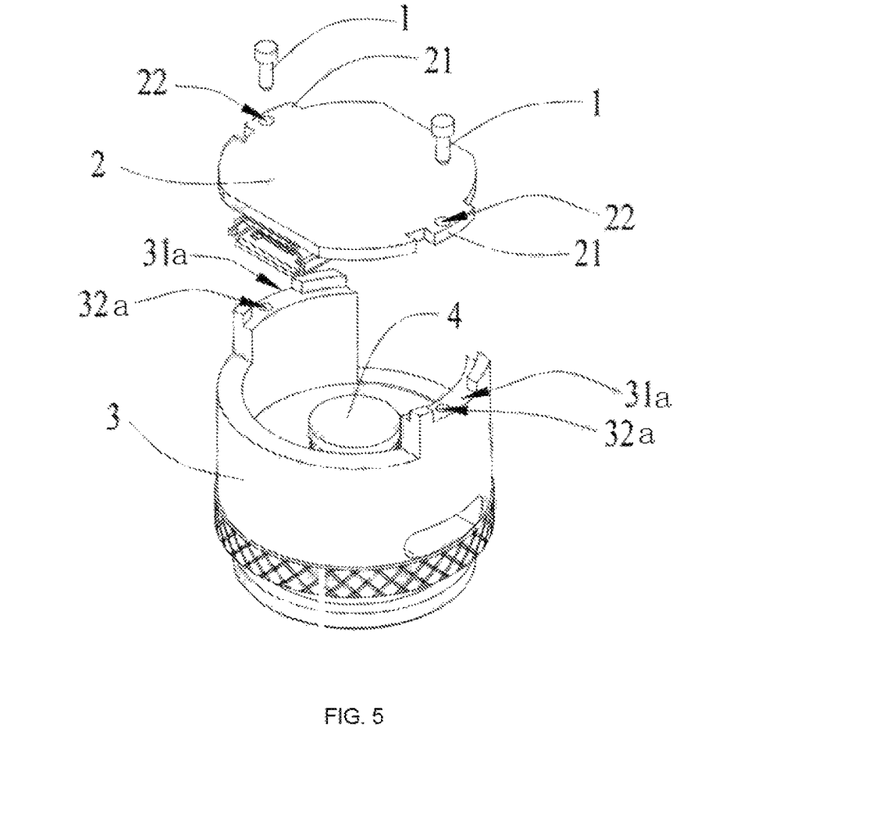
FIG. 5 is an exploded view of a fixing structure for a PCBA control board of an electronic cigarette of the present disclosure.

Referring to FIG. 5, in an embodiment of the present disclosure, the fixing structure includes a PCBA control board 2 and a fixing part 3 configured for fixing the PCBA control board 2. The PCBA control board 2 is configured to be in fixed connection with the fixing part 3 through a conducting nail 1. The conducting nail 1 is configured to be in electric connection with an output negative electrode (not shown in the drawings) of the PCBA control board 1.

According to the present embodiment, the PCBA control board 2 of the electronic cigarette is fixed on the fixing part 3 through the conducting nail 1. Since the conducting nail 1 has no cap, the area of the PCBA control board 2 of the electronic cigarette can be reduced. Moreover, in the present embodiment, since the conducting nail 1 is in electric connection with the output negative electrode of the PCBA control board 2, a space occupied by an output negative electrode wire of the PCBA control board 2 is saved, and then the area of the PCBA control board 2 of the electronic cigarette is reduced. Thus, the electronic cigarette has the size reduced and has a better appearance. The present embodiment has a stable and firm structure, and meanwhile solves the problem of securing the PCBA control board 2 in a narrow and small space of the electronic cigarette.

Further, referring to FIG. 5, FIG. 5 is an exploded view of a fixing structure for a PCBA control board of an electronic cigarette of the present disclosure. In the present embodiment, the fixing part 3 defines a clamping groove 31a configured for clamping the PCBA control board, the PCBA control board 2 is provided with a projecting portion 21 fitting the clamping groove 31a, and the PCBA control board 2 is configured to be clamped in the clamping groove 31a of the fixing part 3 through the projecting portion 21. The structure according to the present embodiment has good firmness.

Further, in the present embodiment, the projecting portion 21 on the PCBA control board 2 defines a through hole 22 fitting the conducting nail 1, the clamping groove 31a has a bottom surface defining a blind hole 32a fitting the conducting nail 1 at a position directly opposite the through hole 22, and the conducting nail 1 is configured for fixing the PCBA control board 2 to the fixing part 3 via the through hole 22 and the blind hole 32a. The present embodiment has simple structure and good firmness, and is easy to implement.

Further, in the present embodiment, the projecting portion 21 of the PCBA control board 2 is provided with a first tin layer (not shown in the drawings) on an end surface facing the bottom surface of the clamping groove 31a, the through hole 22 on the projecting portion 21 has an inner sidewall provided with a second tin layer (not shown in the drawings), both the first tin layer and the second tin layer are configured to serve as the output negative electrode of the PCBA control board 2, the first tin layer and the second tin layer are configured to be in electric connection with the fixing part 3. According to the present embodiment, the fixing part 3 is conducted to the output negative electrode of the PCBA control board 2 through the first tin layer and the second tin layer, and then the assembly mode of the electronic cigarette is simplified. Meanwhile, the electronic cigarette operates more stably and reliably.

Further, in the present embodiment, the conducting nail 1 is provided with a third tin layer (not shown in the drawings) on a top thereof, and the third tin layer is configured for fastening and welding the conducting nail 1 to the PCBA control board 2. The present embodiment further enhances the firmness between the PCBA control board 2 and the fixing part 3.

Further, in the present embodiment, the fixing structure further includes a positive electrode contact component 4 fixed on the fixing part 3, and the PCBA control board 2 has a positive electrode output wire welded to the positive electrode contact component 4.

Further, in the present embodiment, the conducting nail 1 is made of copper materials. Moreover, in the present embodiment, the number of the conducting nails 1, the number of the projecting portions 21 on the PCBA control board 2, the number of the clamping grooves 31a on the fixing part 3, the number of the through holes 22, and the number of the blind holes 32a are two respectively; the projecting portions 21 are configured to be arranged opposite each other at two sides of the PCBA control board 2; and the clamping grooves 31a are configured to be arranged opposite each other at two sides of the fixing part 3. According to the present embodiment, the PCBA control board 2 is fixed on the fixing part 3 through two conducting nails 1. The stability is good. It is understandable that, in other embodiments, the fixing part 3 can define more clamping grooves, the PCBA control board 2 is provided with projecting portions fitting each clamping groove, and each projecting portion of the PCBA control board 2 is configured to be clamped in each clamping groove of the fixing part 3, so that the PCBA control board 2 is fixed firmly in the fixing part 3.

The present disclosure further provides an electronic cigarette. The electronic cigarette includes the fixing structure described above. The construction of the fixing structure can be referred to the above embodiments. No further description is needed here. Since the electronic cigarette of the present embodiment employs the technical scheme of the fixing structure above, the electronic cigarette has all beneficial effects of the fixing structure above.

The above are preferred embodiments of the present disclosure merely and are not intended to limit the patent scope of the present disclosure. Any equivalent structures made according to the description and the accompanying drawings of the present disclosure without departing from the idea of the present disclosure, or any equivalent structures applied in other relevant technical fields directly or indirectly are intended to be included in the patent protection scope of the present disclosure.

What is claimed is:

1. A fixing structure, comprising a housing, a PCB accommodated in the housing, and a top cap covering the housing, wherein the housing has a side wall provided with at least two protrusion portions, each protrusion portion defines a connecting hole, the PCB defines at least two first through holes, the top cap defines at least two second through holes, the fixing structure further comprises at least two connecting pieces, each connecting piece is configured to pass through one of the second through holes, one of the first through holes and one of the connecting holes in sequence so as to fix the top cap and the PCB to the housing.

2. The fixing structure according to claim 1, wherein the PCB comprises a first PCB and a second PCB connected to the first PCB, the first PCB and the second PCB are configured to be arranged opposite each other in parallel, the first PCB defines at least two of the first through holes, the second PCB defines at least two notches at corresponding positions, the protrusion portion is configured to pass through the notch, and the first PCB is configured to be connected to a top end of the protrusion portion.

3. The fixing structure according to claim 1, wherein the housing has two opposing side walls provided with a limiting column respectively, the PCB has an edge defining a plurality of limiting grooves, and each of the limiting columns is configured to be partially accommodated in the limiting groove.

4. The fixing structure according to claim 1, wherein the PCB is provided with a USB interface at one end thereof, and the housing defines an opening matched with the USB interface at a corresponding position thereof.

5. The fixing structure according to claim 1, wherein the PCB is provided with a display on one side close to the top cap, and the top cap is provided with a transparent lens at a position corresponding to the display.

6. The fixing structure according to claim 5, wherein the top cap is further provided with a conducting ring in a convex way at a position far away from the transparent lens, the conducting ring is configured to be in electric connection with the PCB, the PCB defines a mounting hole, and the conducting ring is configured to be partially accommodated in the mounting hole.

7. The fixing structure according to claim 5, wherein the second through hole has a hole wall extending in the direction towards the PCB to form a screw stud, the screw stud is configured to abut against the PCB, the top cap and the PCB form an accommodation portion therebetween, and the display is configured to be accommodated in the accommodation portion.

8. An electronic cigarette, comprising the fixing structure according to claim 1, an atomization assembly, and a big copper part connected to the atomization assembly, wherein the top cap is provided with a conducting ring in a convex way, the top cap defines a hole at a position corresponding to the conducting ring, and the big copper part is configured to pass through the hole to be partially accommodated in the conducting ring.

9. The electronic cigarette according to claim 8, wherein the big copper part is configured to be in electric connection with the conducting ring, and the conducting ring is configured to be in electric connection with the PCB.

10. The electronic cigarette according to claim 8, wherein the electronic cigarette further comprises a battery, and the battery is configured to be connected to one side of the PCB and accommodated in the housing.

* * * * *